United States Patent [19]

Namba et al.

[11] Patent Number: 4,494,549
[45] Date of Patent: Jan. 22, 1985

[54] DEVICE FOR DIAGNOSING BODY CAVITY INTERIORS WITH SUPERSONIC WAVES

[75] Inventors: Akihiro Namba; Mitsugu Sakai, both of Hachioji, Japan

[73] Assignee: Olympus Optical Co., Ltd., Tokyo, Japan

[21] Appl. No.: 377,924

[22] Filed: May 13, 1982

[30] Foreign Application Priority Data

May 21, 1981 [JP] Japan .................. 56-77221

[51] Int. Cl.³ .................. A61B 10/00
[52] U.S. Cl. .................. 128/660; 128/4
[58] Field of Search .................. 128/660-661, 128/663, 4, 6, 24 A

[56] References Cited

U.S. PATENT DOCUMENTS

| | | | |
|---|---|---|---|
| 4,034,744 | 7/1977 | Goldberg | 128/660 |
| 4,280,506 | 7/1981 | Zurcher | 128/690 |
| 4,349,032 | 9/1982 | Koyata | 128/660 |
| 4,374,525 | 2/1983 | Baba | 128/660 |
| 4,375,818 | 3/1983 | Suwaki et al. | 128/660 |
| 4,391,282 | 7/1983 | Ando et al. | 128/660 |

OTHER PUBLICATIONS

Taylor, W. B. et al. "A High-Resolution Transrectal UTS System", UTS in Med. & Biol., pp. 129-138, Pergamon Press, 1979.
Baba, K. "Ultrasonic Scanner for Examination of a Coeliac Cavity", Europ. Patent Application Publ. No. EP0028825 published 5-81.

Primary Examiner—Kyle L. Howell
Assistant Examiner—Francis J. Jaworski
Attorney, Agent, or Firm—Armstrong, Nikaido, Marmelstein & Kubovcik

[57] ABSTRACT

A device for diagnosing the interior of a body cavity is described which includes an optical endoscope, and a supersonic wave scanner probe which may be physically and operatively attached thereto. The supersonic wave scanner may be used with the optical endoscope, or may be detached and replaced by a hemispherical lid whereupon the endoscope may be inserted into the body cavity for optical observations only.

2 Claims, 4 Drawing Figures

DEVICE FOR DIAGNOSING BODY CAVITY INTERIORS WITH SUPERSONIC WAVES

BACKGROUND OF THE INVENTION

This invention relates to a device for diagnosing body cavity interiors with supersonic waves wherein a supersonic wave scanner part containing apparatus of transmitting and receiving supersonic waves is removably fitted on the tip of an endoscope having illuminating and observing optical systems arranged on the tip of a part to be inserted into a body cavity.

A supersonic wave diagnosing device wherein supersonic waves are transmitted and received to use acoustic information within a body cavity for a diagnosis has heretofore been used together with an endoscope wherein an inserted part can be inserted into a body cavity to optically observe the body cavity interior or to make a therapeutic treatment by using a forceps.

There are presently diagnosing devices using supersonic waves wherein supersonic wave pulses are projected into a living body from the surface of the living body and reflected waves from various organs within the living body are received to observe the movements of the abdominal part, heart and others, and also supersonic wave diagnosing devices for body cavity interiors wherein a part for transmitting, receiving and scanning supersonic waves is inserted into a body cavity to obtain reflected waves of the supersonic waves from a position near to an objective internal organ within the body cavity.

As compared with the former wherein supersonic wave pulses are projected from the surface of a living body, the latter is used in a position near to an objective internal organ, and the supersonic waves can be used at a high frequency that would normally attenuate greatly with an increase of the because distance, no unnecessary part of the body is interposed. Therefore the influence of the reflected waves from the unnecessary part can be avoided and therefore there is an advantage that a picture image high in resolving power and quality can be obtained.

Therefore, there has been developed a device for diagnosing body cavity interiors with supersonic waves wherein the above mentioned part transmitting, receiving and scanning supersonic waves for a supersonic wave diagnosis is inserted into a body cavity so that the position within the body cavity where the above mentioned part of the device is located can be determined and the body cavity interior can be optically observed.

As prior art examples of the above mentioned devices for diagnosing body cavity interiors with supersonic waves, there are such disclosures as, for example, in the Gazettes of Japanese Patents Laid Open Nos. 129026/1980 and 148530/1980. However, each of them has it as a primary object to transmit supersonic waves from a body cavity interior to an internal organ within the body cavity to obtain a supersonic wave cross-sectioned image and therefore a part of the function of the ordinary endoscope will be impaired. One of the greatest disadvantages is that the supersonic wave scanner part transmitting, receiving and scanning supersonic waves is added to the tip of the inserted part of the endoscope and the part which can not be bent at the tip is longer by about 30 mm. than that of an ordinary endoscope. Therefore, when the endoscope is to be inserted, the pain of the patient will be increased and the operability of the endoscope within the body cavity will be reduced. For these reasons, it is inconvenient to use an endoscope having a supersonic wave diagnosing function for an ordinary endoscope inspection, an endoscope exclusively for observation must be prepared and therefore there has been a problem that the economic burden will be large.

BRIEF SUMMARY OF THE INVENTION

An object of the present invention is to provide a device for diagnosing body caivty interiors with supersonic waves wherein a supersonic wave scanner device for transmitting and receiving supersonic waves arranged on the tip of illuminating and observing optical systems of an inserted part is made removable so that the device can be used not only as a body cavity interior supersonic wave diagnosing device but also as an endoscope which is easy to operate.

Another object of the present invention is to removably construct a supersonic wave scanner part so that the maintenance and repair may be easy and the burden of the cost of replacing broken parts may be reduced.

The objects, features and advantages of the present invention will be made apparent enough by the following explanation.

BRIEF DESCRIPTION OF THE DRAWINGS

FIG. 1 is a vertically sectioned view showing essential parts on the tip of an inserted part of a device for diagnosing body cavity interiors with supersonic waves in the prior art example.

FIG. 2 is a perspective view with a balloon removed of the prior art device shown in FIG. 1.

FIG. 4 is a verical sectional view showing a lid part in the embodiment.

DETAILED DESCRIPTION OF THE INVENTION

Figure 1:
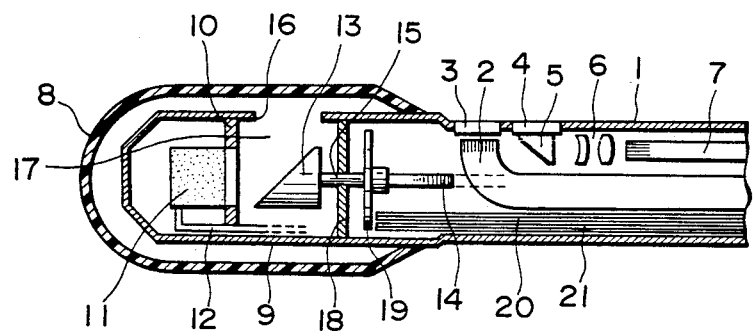
FIGS. 1 and 2 relate to a prior art example.
Figure 2:
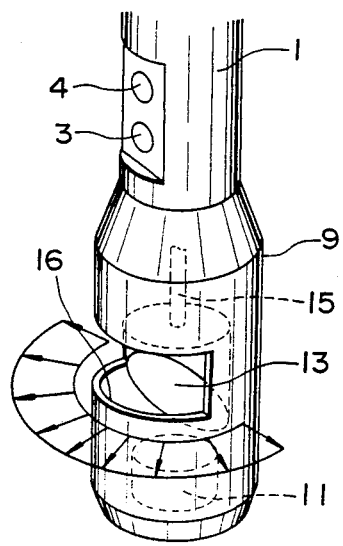

Prior to explaining the embodiment of the present invention, the conventional example of the device for diagnosing body cavity interiors with supersonic waves shall be described with reference to FIGS. 1 and 2.

In these drawings, a tubular inserted part 1 is formed of a flexible member, an illuminating optical system and observing optical system are arranged in the tip part of this inserted part and a function of transmitting and receiving supersonic waves is contained in a balloon covering a hard outer tube fitted to the front end of this tip part.

A flexible light guide 2 formed of a glass fiber bundle or the like transmitting an illuminating light from an external light source not illustrated is inserted through the above mentioned inserted part and is curved at the tip and a glass window 3 is provided through the inserted part 1 in front of the end surface of the curved light guide 2 so that the illuminating light may be projected into a body cavity through this glass window 3.

On the other hand, for an optical system for observing an internal organ or the like illuminated by the illuminating light, a glass window 4 is provided substantially adjacently to the above mentioned glass window 3 on the inserted part 1, a right angle prism 5 is contained in contact with the inside of the glass window 4, a focusing lens system 6 for focusing the incident light reflected at right angles through the prism 5 and an image guide 7 formed of a fine glass fiber bundle or the like to transmit the optical image focused by the focusing lens system 6 are contained in the inserted part 1 so that the optical image can be observed from outside the rear end of an eyepiece part not illustrated through this image guide 7.

On the other hand, a bag-shaped balloon 8 projecting forward in the tip part of the inserted part 1 is formed of such material as rubber or organic resin which can effectively transmit and receive supersonic wave beams in close contact directly with such living body part as a stomach wall and contains a hard outer tube made of a metal or the like.

This outer tube 9 contains a supersonic wave oscillator 11 supported by a supporting member 10 fixed on the periphery in contact with the inner peripheral surface of the outer tube 9 to generate and receive supersonic waves and convert them to electric signals, a signal cable 12 connected to this supersonic wave oscillator to transmit the electric signals, a supersonic wave mirror 13 Positioned to reflect supersonic wave beams and transmit them a right angles, and a hard shaft 15 rotating the above mentioned supersonic wave mirror 13 through a curvable coil wire 14 transmitting the rotation by a motor provided outside.

The above mentioned supersonic wave oscillator 11 is formed of such piezoelectric material as quartz or PZT (a solid solution of lead zirconate $PbZrO_3$ and lead titanate $PbTiO_3$) to generate supersonic waves when electric signals are impressed or to generate electric signals when excited by supersonic waves. The supersonic wave mirror 13 having a reflecting surface reflecting supersonic wave beams substantially at right angles as inclined by 45 degrees is arranged opposite the transmitting and receiving surface of this supersonic wave oscillator 11. An opening 16 is provided on the outer tube 9 along the rotation transmitting and receiving surface of this supersonic wave mirror 13 so that the supersonic wave beams generated by the above mentioned supersonic wave oscillator 11 can be projected (transmitted) in directions in a wide range (such as, for example, of about 180 degrees) by the rotation of the supersonic wave mirror 13. Further, the transmitting and receiving surface of the supersonic wave oscillator 11 and the periphery of the supersonic wave mirror 13 are filled with such supersonic wave transmitting medium 17 having a value substantially equal to the acoustic impedance of an internal organ or the like within a living body as water or olive oil so that the supersonic waves can be effectively transmitted. The interior of the balloon 8 is filled with this transmitting medium 17 through the above mentioned opening 16. This transmitting medium 17 is sealed and intercepted by a sealing material 18 so as to be prevented from leaking on the observing optical system side.

A disk indicated by the reference numeral 19 is fixed to the shaft 15 so as to rotate integrally with the supersonic wave mirror 13, has a reflecting part of fine filaments provided on one surface and has two optical fibers 20 and 21 arranged opposite this reflecting part. This optical fiber 20 is to lead a light from the external light source and illuminate the surface on which the above mentioned reflecting part is provided of the disk 19 and, on the other hand, the other optical fiber 21 is to transmit the light reflected by the reflecting part to external controlling and treating means (not illustrated) so that the beginning of the sector-scanning of the supersonic waves can be marked by the signal of the reflected light.

However, in the above mentioned conventional example, as the hard outer tube 9 part containing the apparatus for transmitting and receiving supersonic waves is fitted on the extreme front end of the illuminating and observing optical systems arranged in the tip part of the inserted part 1, there have been problems that, when the device is to be used as an optically observing endoscope, and it is inserted toward an objective position within a body cavity, the above mentioned hard outer tube 9 part will be in the way, the tip part of this outer tube 9 will contact an internal organ or the like and will cause a pain to the patient and, when the objective position within the body cavity is to be observed, the operator will find it difficult to operate the device.

The present invention is made to solve the problems of the above mentioned conventional example.

The device for diagnosing body cavity interiors with supersonic waves embodying the present invention shall be described in the following with reference to FIGS. 3 and 4.

Figure 3:
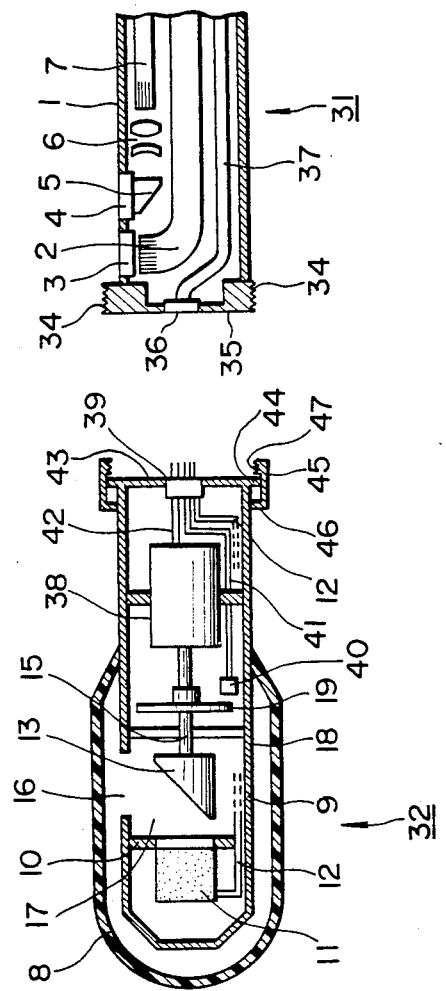
FIGS. 3 and 4 are vertical sectional views showing essential parts of the tip of an inserted part of an embodiment of the present invention.
Figure 4:
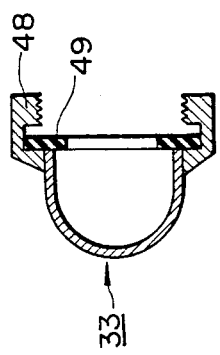

The embodiment shown in FIGS. 3 and 4 is formed of a first part (which shall be called an endoscope part hereinafter) corresponding to an ordinary endoscope and a second part (which shall be called a scanner part hereinafter) for transmitting, receiving and scanning supersonic waves. The same respective reference numerals shall be attached to the parts (elements) of the same formation as of the conventional example except that the endoscope part and scanner part are made separable from each other and some of them shall not be explained.

In the endoscope part 31, the construction of the inserted part of the reference numeral 1 to the image guide of the reference numeral 7 is exactly identical with the construction of the above described conventional example and therefore shall not be explained.

A connecting part 35 made of a metal or the like and provided with an engaging screw 34 along the outer tube 9 is formed at the tip of the inserted part 1 so that a scanner part 32 and such lid part 33 as is shown in FIG. 4 can be fitted and removed. An electrically connecting connector (receptacle) 36 is fitted substantially in the center of the connecting part 35. Cables 37 are connected to the respective terminals of this connector 36, are contained in the inserted part 1 and are connected at the other ends to the external controlling and treating means (not illustrated).

In the scanner part 32, the main differences from the conventional example are that a motor 38 is contained in the outer tube 9, that a connector (plug) 39 to be connected with the above mentioned connector 36 is provided and fixed at the rear end of the outer tube 9 and that means of connecting and fixing the scanner part 32 to the above mentioned endoscope part 31 are provided.

That is to say, the same as in the conventional example, the outer tube 9 is contained in the balloon 8 and further the supersonic wave oscillator 11 fixed with the supporting member 10, the signal cable 12 connected to this oscillator 11, the supersonic wave mirror 13 reflecting supersonic wave beams and scanning them at right angles, the hard shaft 15 for rotating this supersonic wave mirror 13, the supersonic wave transmitting medium 17 and the disk 19 for generating starting pulses are contained in this outer tube 9 as arranged as described above.

A motor 38 is contained in this outer tube 9. The rotary shaft of this motor 38 is connected directly to the other end of the above mentioned shaft 15 so as to be able to rotate and drive the supersonic wave mirror 13.

Further, a photoreflector 40 provided with such light emitting element as a light emitting diode and such light receiving element as a phototransistor (having the same functions as of the optical fibers 20 and 21 of the conventional example) in parallel.

This photoreflector 40 will illuminate the disk 19 provided with the light reflecting part with the light emitting element and the light reflected by the reflecting part will be received by the light receiving element to put out electric pulses. This photoreflector 40, the current source for emitting the light and a cable 41 transmitting electric pulse signals, the signal cable 12 for the supersonic wave oscillator 11 and a cable 42 feeding an electric power for driving the motor 38 are connected to the respective terminals of the connector 39 provided substantially in the center of a scanner joining part 43 at the rear end of the outer tube 9 so as to be connected to the external controlling and treating means (not illustrated) through the cables 37 within the inserted part 1 on the endoscope 31 when the connector 39 is connected with the connector 36 on the endoscope part 31.

The joining part 43 at the rear end of the above mentioned outer tube 9 is provided radially with an engaging projection 44. A ring-shaped fixing piece 45 is annularly fitted to the outer periphery of this projection 44. In the front end part of this fixing piece 45, an engaging part 46 is provided to project inward so as to be able to be engaged with the projection 44 of the above mentioned scanner joining part 43. A screw 47 to be screwed with the screw 34 of the above mentioned endoscope part 31 is formed inside the rear end part of the fixing piece 45. This ring-shaped fixing piece 45 is made somewhat movable in the lengthwise direction on the surface of the outer tube 9 so as to slide on the inner peripheral surface with the projection 44. The scanner part 32 can be easily fixed to the endoscope part 31 with this fixing piece 45 by inserting and connnecting the connector 39 to the connector 36, then rotating the fixing piece 45 and rotating the screw 47 inside the other end of the fixing piece 45 so as to be screwed with the screw 34 of the endoscope part 31 as the engaging part 46 formed in one end part of the fixing piece 45 is so formed as to be engaged with the projection 44 at the rear end of the scanner part 32.

In removing the scanner part 32, if the fixing piece 45 is rotated in the direction reverse to the above, both screws 34 and 47 will be disengaged from each other and, if a force is applied in the direction of separating the scanner part 32 and endoscope part 31 from each other, the scanner part 32 will be easily removed. On the other hand, in case the endoscope part 31 is to be used alone as an endoscope, when the endoscope part 31 is inserted into a body cavity, the screw 34 on the periphery of the connecting part 35 at the tip will be likely to injure the structure within the body cavity. Therefore, such lid part 33 as is shown in FIG. 4 is fitted to prevent any injury. This lid part 33 is formed to be substantially hemispherical at the tip so as to be able to be inserted smoothly into the body cavity. A lid joining part 48 is provided at the rear end of the lid part 33. A screw to be screwed with the screw 34 formed on the joining part 35 at the tip of the endoscope part 31 is formed on the inner peripheral surface on the rear end of this lid joining part 48. A ring-shaped recess is formed on the inner peripheral surface adjacent to the part on which the screw is formed of the lid joining part 48. An annular elastic packing material 49 which has a hole in the center is contained in this recess.

On the other hand, even in the engagement of the scanner part 32 and endoscope part 31 shown in FIG. 3 with each other, so that no water may leak in the case of washing or the like, for example, the part of the scanner joining part 43 or projection 44 is painted with grease or the annular packing material 49 provided in the lid part 33 is so formed as to be able to well prevent leakage of water (not illustated).

The operation of the embodiment of the present invention formed as in the above shall be described in the following.

First, in the case of using the device as an endoscope, the lid part 33 shown in FIG. 4 is fitted to the tip of the endoscope part 31. In fitting it, when the lid joining part 48 of the lid part 33 is fitted to the connecting part 35 formed at the tip of the endoscope part 31 and the lid part 33 is rotated, the screw of the lid joining part 48 will be screwed with the screw 34 formed on the connecting part 35 and the end surface of the connecting part 35 will press the packing material 49 within the lid part 48 so that the lid part 33 will be elastically strongly fixed.

The endoscope part 31 fitted with the lid part 33 can be used as an ordinary side seeing type endoscope.

In the operation of this use, when the endoscope part 31 is inserted into a body cavity, an illuminating light by the light source fed from the end surface on the right hand side not illustrated of the light guide 2 will be led by the light guide 2 to illuminate the body cavity interior from the surface of the curved tip of the light guide. This illuminating light will be reflected by various internal organs or the like within the body cavity and will form optical images of the internal organs or the like within the body cavity on the tip surface of the image guide 7 through the prism 5 provided in close contact with the glass window 4 and the focusing lens system 6. These optical images will be led to the eyepiece part on the right hand side not illustrated through the image guide 7 so that the observer will be able to observe the body cavity interior by seeing the end surface of the image guide 7.

In such case, as the lid part 33 is only formed at the tip of the endoscope part 31, there will be advantages that any pain caused to the patient will be able to be reduced and the operation within the body cavity will be easier than in inserting the endoscope part 31 as fitted with the scanner part 32 into the body cavity.

On the other hand, in the case of using the device as a body cavity interior supersonic wave diagnosing device, the lid part 33 is rotated and removed and the scanner part 32 is fitted. To fit it, as described above, the connector (plug) 39 on the scanner part 32 side may be inserted and connected to the connector (receptable) 36 on the endoscope part 31 and then the fixing piece 45 may be rotated to screw the screws 47 and 34 respectively on the scanner part 32 and endoscope part 31 with each other.

With the above mentioned endoscope part 31, various internal organs within a body cavity are observed and the balloon 8 is brought into close contact with a desired internal organ. In this state, electric power will be fed to the motor 38 to rotate the supersonic wave mirror 13, transmitting electric pulses will be put out of the external transmitting circuit (not illustrated) with the pulse detected by the photoreflector 40 as a reference and the supersonic wave oscillator 11 will be thereby excited through the signal cable 12 to project supersonic wave beams out of the transmitting and receiving surface of the oscillator. The supersonic wave beams projected out of the above mentioned transmitting and receiving surface will be reflected by the supersonic wave mirror 13, will pass through the opening 16, will further pass through the balloon 8 covering the opening 16 and will be sector-scanned toward the living body in close contact with and outside the balloon 8. The supersonic wave beams projected into the living body on will be reflected by the boundary surface on which the acoustic impedance of the substance forming the living body structure is different and will again excite the supersonic wave oscillator 11 through the balloon 8, supersonic wave transmitting medium 17 and supersonic wave mirror 13. The piezoelectric oscillation by this supersonic wave oscillator 11 will generate electric signals at the electrodes attached to both ends of the supersonic wave oscillator 11. These electric signals will be fed to the external controlling and treating means (not illustrated) through the signal cable 12, will be synchronized with the sweep signal having as a reference the pulse detected by the photoreflector 40 and will indicate a supersonic wave cross-sectional image of the living body in such indicating means as a Braun tube.

It is a great advantage of the present invention that the endoscope part 31 can be used as fitted with the scanner part 32 substantially the same as the conventional example made integral with the scanning part 32 and can be used also with the scanner part 32 removed as an ordinary endoscope easy to operate.

In the above mentioned embodiment, the photoreflector 40 which is easy to connect with the scanner part 32 functions exactly the same as the optical fibers 20 and 21 used in the conventional example but is made removable. The signals produced by this photoreflector 40 can be transmitted by the cables 37 made integral the same as the lines for transmitting other signals through the inserted part 1. Therefore an inserting path or guide channel as is needed in the case of the optical fibers need not be formed within the inserted part and thus there are advantages that the structure of the inserted part can be simplified and that the cost of it can be reduced.

Further, as the motor 38 is contained in the scanner part 32, there are advantages that it is no longer necessary to insert the coil wire 14 for transmitting the rotary drive through the long inserted part 1 and that the inserted part 1 can be simplified in the structure, can be made small in diameter and can reduce the pain caused to the patient when it is inserted into a body cavity.

Further, as the scanner part 32 is made removable, there are advantages that the maintenance and repair are easy and that broken parts can be easily replaced.

By the way, though no treating tool inserting hole is illustrated in the endoscope part 31 in the present invention, it is needless to say that a treating tool inserting hole can be provided so as to give a treating function. Further, in the above mentioned embodiment, the motor 38 is provided as a scanning means within the scanning part 32 but it is also possible that supersonic wave beams are scanned to make a reciprocating rotary motion by a driving part formed by providing a rotatable coil between two permanent magents and attaching a spiral spring (not illustrated) to the shaft of this coil so as to feed an alternating current to this coil to reciprocally rotate the supersonic wave mirror 13.

Further, in the above mentioned embodiment, it is shown that the scanner part 32 and endoscope part 31 are removable from each other by screwing. However, the present invention is not limited to it. It is needless to say that such means as, for example, bayonet-mounting or the like may be used.

Also, in the above mentioned embodiment, the motor 38 for rotating and driving the supersonic wave mirror 13 is contained in the scanner part 32 but may be provided outside and its driving shaft may be inserted through the inserted part 1 so as to be present at the tip of the inserted part 1 and to be connected with the supersonic wave mirror 13 shaft side on the scanner part 32 side when the endoscope part 31 and scanner part 32 are connected with each other.

It is apparent that working modes different in a wide range can be formed without departing from the spirit and scope of the present invention.

The above mentioned working modes other than are limited in the claims in the present invention shall be included in the scope of the present invention.

We claim:

1. A device for diagnosing the interior of a body cavity comprising:
   an optical endoscope part adapted to be inserted into said body cavity;
   a supersonic wave scan head assembly adapted to be inserted into said body cavity and attached distal to said optical endoscope part; and
   connecting means arranged on said endoscope part and on said supersonic wave scan head assembly for removably physically and operatively attaching said supersonic wave scan head assembly distal to the end of said endoscope part, a lid part having connecting means thereon adapted for connection to said optical endoscope part whereby said lid part may be removably attached to said endoscope part connecting means when said supersonic wave scan head assembly is detached therefrom, whereby said endoscope part may be used with said supersonic wave scan head assembly attached thereto for both optical observations and supersonic wave diagnosis within a body cavity and may be used within a body cavity for optical observations only with said supersonic wave scan head assembly detached.

2. A device as claimed in claim 1 wherein said lid part is of substantially hemispherical shape and is arranged to seal said means for operatively attaching said supersonic wave scan head assembly and to facilitate insertion of said endoscope part into said body cavity, whereby said endoscope part is more readily inserted into said body cavity when said supersonic wave scan head assembly is detached therefrom and said lid part is attached thereto.

* * * * *